US009132229B2

(12) United States Patent
Gao et al.

(10) Patent No.: US 9,132,229 B2
(45) Date of Patent: Sep. 15, 2015

(54) SYSTEM AND METHOD OF PRIMING A SURGICAL CASSETTE

(75) Inventors: Shawn X. Gao, Irvine, CA (US); Roderick S. Van, Long Beach, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 257 days.

(21) Appl. No.: 13/614,745

(22) Filed: Sep. 13, 2012

(65) Prior Publication Data
US 2014/0074017 A1 Mar. 13, 2014

(51) Int. Cl.
| | |
|---|---|
| A61M 1/00 | (2006.01) |
| A61M 5/142 | (2006.01) |
| F04D 9/00 | (2006.01) |
| A61M 1/28 | (2006.01) |
| A61M 5/14 | (2006.01) |
| A61M 1/36 | (2006.01) |
| A61M 5/31 | (2006.01) |

(52) U.S. Cl.
CPC ............... *A61M 5/142* (2013.01); *F04D 9/004* (2013.01); *A61M 1/288* (2014.02); *A61M 1/3643* (2013.01); *A61M 1/3644* (2014.02); *A61M 1/3647* (2014.02); *A61M 5/3146* (2013.01); *A61M 2005/1402* (2013.01)

(58) Field of Classification Search
CPC . A61M 1/288; A61M 1/3643; A61M 1/3644; A61M 1/3646; A61M 1/3647; A61M 1/3649; A61M 1/0058; A61M 1/3629; A61M 2005/1402; A61M 5/3146
USPC .......................... 604/28, 22, 19, 140, 30, 500
See application file for complete search history.

(56) References Cited

U.S. PATENT DOCUMENTS

| | | | |
|---|---|---|---|
| 3,589,363 A | 6/1971 | Banko | |
| 4,041,947 A | 8/1977 | Weiss | |
| 4,223,676 A | 9/1980 | Broadwin | |
| 4,246,902 A | 1/1981 | Martinez | |

(Continued)

FOREIGN PATENT DOCUMENTS

| | | |
|---|---|---|
| EP | 0717970 A1 | 6/1996 |
| EP | 1310267 A2 | 5/2003 |

(Continued)

OTHER PUBLICATIONS

PCT/US2013/055287, International Search Report and Written Opinion; International Searching Authority, Aug. 16, 2013, 7 pgs.

(Continued)

*Primary Examiner* — Bhisma Mehta
*Assistant Examiner* — Nilay Shah

(57) ABSTRACT

The present disclosure relates in general to an apparatus and method for priming a liquid or surgical cassette. In one embodiment, an infusion system within the liquid cassette is primed using a forward flow of a liquid and a backward flow of the liquid. The forward flow of the liquid creates a first volume of liquid stored within an infusion conduit, which is connected to an infusion chamber via a first valve. The infusion conduit has an infusion port exposed to a non-liquid environment having a first pressure. A second pressure is created in the infusion chamber that is lower than the first pressure. Opening the first valve causes a second volume of liquid within the infusion conduit to flow over the first valve and towards the infusion chamber. The second volume of liquid is less than or equal to the first volume of liquid.

14 Claims, 8 Drawing Sheets

(56) References Cited

U.S. PATENT DOCUMENTS

| | | | |
|---|---|---|---|
| 4,465,470 A * | 8/1984 | Kelman | 604/27 |
| 4,493,694 A | 1/1985 | Wuchinich | |
| 4,515,583 A | 5/1985 | Sorich | |
| 4,548,205 A | 10/1985 | Moorhead | |
| 4,589,415 A | 5/1986 | Haaga | |
| 4,609,368 A | 9/1986 | Dotson, Jr. | |
| 4,722,350 A | 2/1988 | Moorhead | |
| 4,841,984 A | 6/1989 | Moorhead | |
| 4,869,715 A | 9/1989 | Sherburne | |
| 4,919,649 A * | 4/1990 | Timothy et al. | 604/65 |
| 4,922,902 A | 5/1990 | Krawitt | |
| 4,989,583 A | 2/1991 | Hood | |
| 4,998,914 A | 3/1991 | Fuchs | |
| 5,106,367 A | 4/1992 | Gaspar | |
| 5,154,694 A | 10/1992 | Kelman | |
| 5,213,569 A | 5/1993 | Davis | |
| 5,267,956 A | 12/1993 | Beuchat | |
| 5,267,964 A * | 12/1993 | Karg | 604/141 |
| 5,359,996 A | 11/1994 | Hood | |
| 5,364,342 A | 11/1994 | Beuchat | |
| 5,494,530 A | 2/1996 | Graf | |
| 5,499,969 A | 3/1996 | Beuchat | |
| 5,556,378 A | 9/1996 | Novak | |
| 5,586,973 A | 12/1996 | Lemaire | |
| 5,609,576 A | 3/1997 | Butterfield | |
| 5,899,674 A | 5/1999 | Nazarifar | |
| 5,910,110 A | 6/1999 | Bastable | |
| 6,224,583 B1 * | 5/2001 | Perkins et al. | 604/408 |
| 6,261,283 B1 | 7/2001 | Sorensen | |
| 6,293,926 B1 | 9/2001 | Sorensen | |
| 6,632,214 B2 | 10/2003 | Sorensen | |
| 6,740,074 B2 | 5/2004 | Sorensen | |
| 6,875,194 B2 | 4/2005 | MacKool | |
| 6,986,753 B2 | 1/2006 | Bui | |
| 7,524,299 B2 * | 4/2009 | Hopkins et al. | 604/30 |
| 7,604,615 B2 * | 10/2009 | Gao et al. | 604/122 |
| 7,713,237 B2 | 5/2010 | Nazarifar | |
| 7,896,839 B2 | 3/2011 | Thomas | |
| 7,981,073 B2 * | 7/2011 | Mollstam et al. | 604/28 |
| 2002/0019607 A1 | 2/2002 | Bui | |
| 2003/0190244 A1 | 10/2003 | Leukanech | |
| 2003/0201412 A1 | 10/2003 | Brody | |
| 2003/0204166 A1 | 10/2003 | Sorensen | |
| 2003/0225366 A1 | 12/2003 | Sorensen | |
| 2004/0089080 A1 | 5/2004 | Steen | |
| 2004/0167462 A1 | 8/2004 | MacKool | |
| 2004/0187613 A1 | 9/2004 | Phillips | |
| 2004/0253129 A1 | 12/2004 | Sorensen | |
| 2005/0080375 A1 | 4/2005 | Kadziauskas | |
| 2006/0058811 A1 | 3/2006 | Kimura | |
| 2007/0010730 A1 | 1/2007 | Gordon | |
| 2007/0135752 A1 * | 6/2007 | Domash et al. | 604/19 |
| 2007/0219494 A1 | 9/2007 | Gao et al. | |
| 2008/0006096 A1 | 1/2008 | Morgan | |
| 2008/0033349 A1 | 2/2008 | Suzuki | |
| 2008/0103433 A1 | 5/2008 | Nazarifar et al. | |
| 2009/0018488 A1 | 1/2009 | Sorensen | |
| 2009/0270793 A1 | 10/2009 | Domash et al. | |
| 2010/0030134 A1 * | 2/2010 | Fitzgerald et al. | 604/34 |
| 2011/0054385 A1 * | 3/2011 | Eichler | 604/22 |

FOREIGN PATENT DOCUMENTS

| | | |
|---|---|---|
| EP | 2014266 A1 | 1/2009 |
| EP | 2014266 B1 | 12/2009 |
| JP | 08-273659 | 10/1996 |
| JP | 09-171401 | 6/1997 |
| WO | 9640026 A1 | 12/1996 |
| WO | 2007001859 A2 | 1/2007 |
| WO | 2007001929 A2 | 1/2007 |
| WO | 2007001929 A3 | 3/2007 |
| WO | 2007001859 A3 | 11/2007 |

OTHER PUBLICATIONS

Prior Art Statement, Aug. 11, 2010.

* cited by examiner

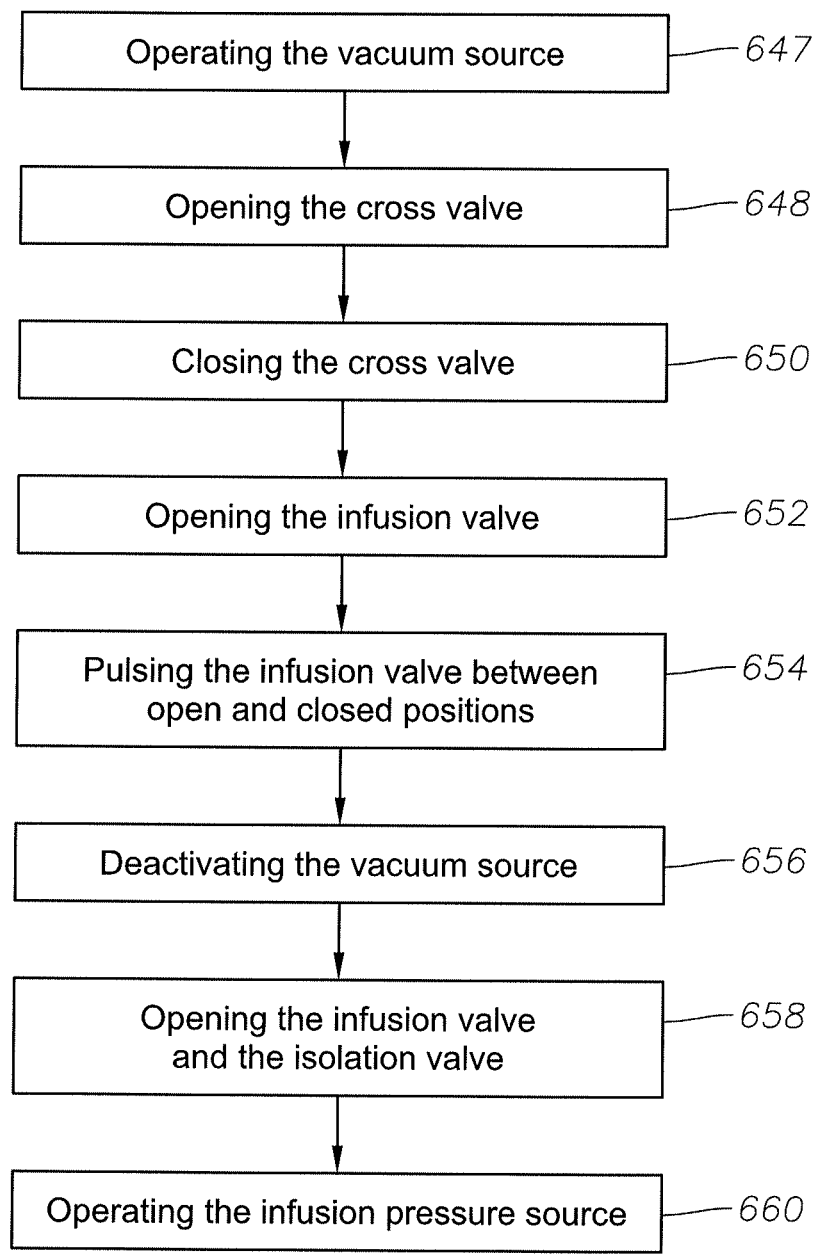

SYSTEM AND METHOD OF PRIMING A
SURGICAL CASSETTE

BACKGROUND

During small incision surgery, and particularly during ophthalmic surgery, small probes are inserted into the operative site to cut, remove, or otherwise manipulate tissue. During these surgical procedures, fluid is typically infused into the eye using an infusion system, and the infusion fluid and tissue are aspirated from the surgical site using an aspiration system. The infusion and aspiration systems must be primed prior to surgery. Gas can become trapped within the infusion system and the aspiration system, which can cause certain problems. In prior systems, the system and method of priming the surgical cassette did not remove the trapped gas from the systems. Therefore, a need continues to exist for an improved system and method of priming a surgical cassette.

SUMMARY

The present disclosure relates in general to an apparatus and method for priming a liquid or surgical cassette. In one embodiment, an infusion system within the liquid cassette is primed using a forward flowing liquid and backward flowing liquid. In one embodiment, the apparatus comprises an infusion chamber configured to receive an infusion liquid from a liquid source via a source valve; an infusion pressure source connected to the infusion chamber via an isolation valve; an infusion conduit connected to the infusion chamber, the infusion conduit having a first valve, the infusion conduit, which can include an infusion tube, having an infusion port exposed to a non-liquid environment having a first pressure; a cross conduit intersecting the infusion conduit at a location between the infusion chamber and the first valve, the cross conduit connected to a vacuum source, the cross conduit having a second valve; and a controller electrically coupled to the first valve, the second valve, the source valve, the isolation valve, infusion pressure source and the vacuum source, the controller controls the opening and the closing of the first valve, the second valve, the isolation valve, and the source valve and also controls the activation of the vacuum source and the pressure source. The controller opens the source valve to fill the infusion chamber first, and then opens the first valve and the second valve to allow the infusion liquid to fill the infusion conduit with a first volume of the infusion liquid, and to at least partially fill the infusion chamber and the cross conduit with the infusion liquid. The controller closes the first, second, source, and the isolation valves to isolate the infusion chamber. The controller operates the vacuum source to create a second pressure in the aspiration chamber. The controller then opens the second valve to create the second pressure in the infusion chamber, the second pressure being lower than the first pressure. The controller opens the first valve and the second valve or the first valve only to allow a second volume of the infusion liquid contained in the infusion conduit to move over the first valve; and wherein the second volume of the infusion liquid is less than or equal to the first volume of the infusion liquid.

BRIEF DESCRIPTION OF THE DRAWINGS

FIG. 6B is a flow chart illustration of a method of operating the system of FIG. 5, according to an exemplary embodiment.

DETAILED DESCRIPTION

Figure 1:
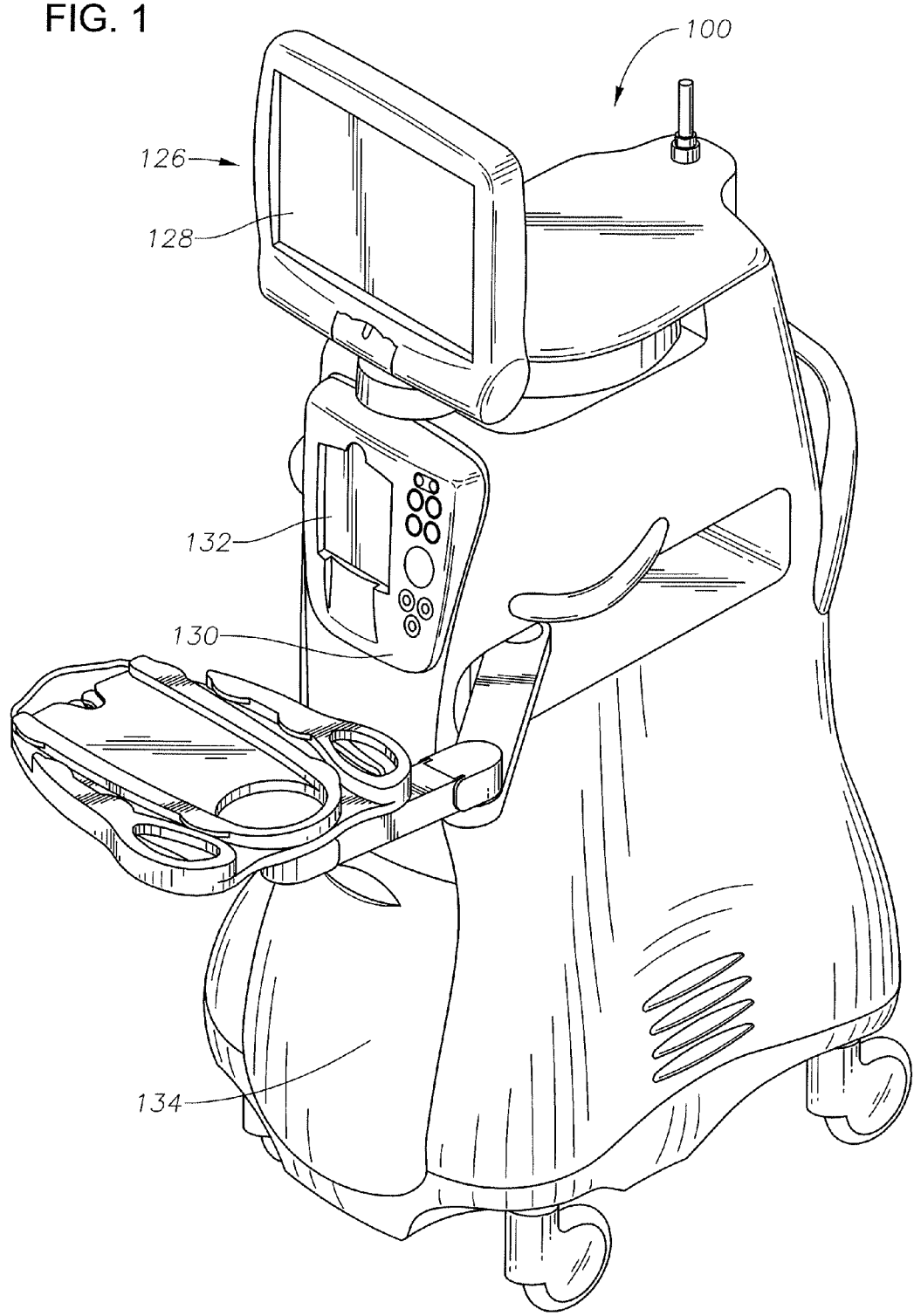
FIG. 1 is a diagrammatic representation of one embodiment of a surgical console.

The following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

In an exemplary embodiment, as illustrated in FIG. 1, an ophthalmic surgical console is generally referred to by the reference numeral 100. The surgical console 100 can include a swivel monitor 126 that has a touch screen 128. The swivel monitor 126 can be positioned in a variety of orientations for whomever needs to see the touch screen 128. The swivel monitor 126 can swing from side to side, as well as rotate and tilt. The touch screen 128 provides a graphical user interface ("GUI") that allows a user to interact with the console 100.

The surgical console 100 also includes a connection panel 130 used to connect various tools and consumables to surgical console 100. The connection panel 130 can include, for example, a coagulation connector, connectors for various hand pieces, and a cassette receiver 132. The surgical console 100 can also include a variety of user friendly features, such as a foot pedal control (e.g., stored behind a panel 134) and other features.

Figure 2:
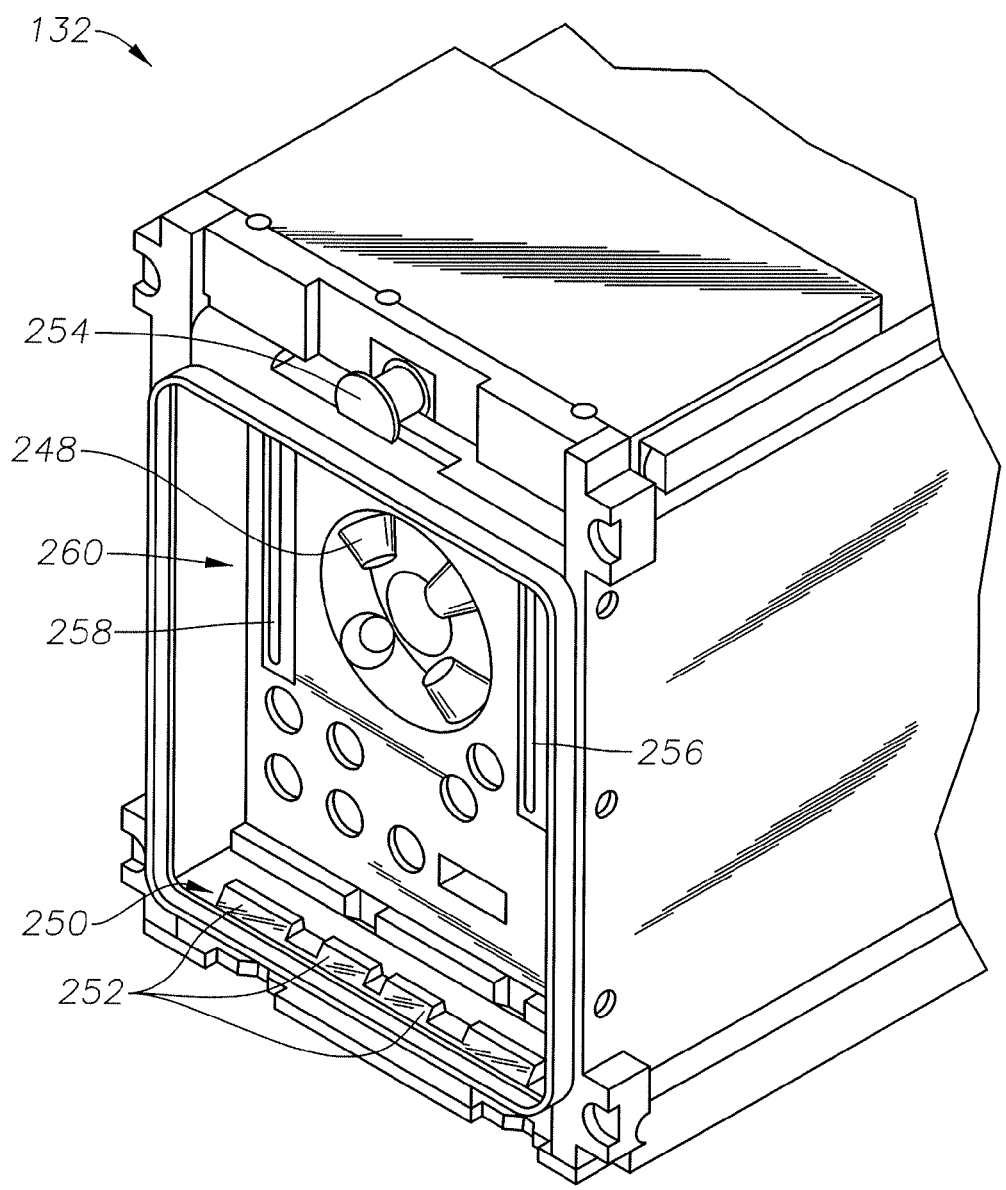
FIG. 2 is a diagrammatic representation of one embodiment of a cassette receiver.
Figure 3:
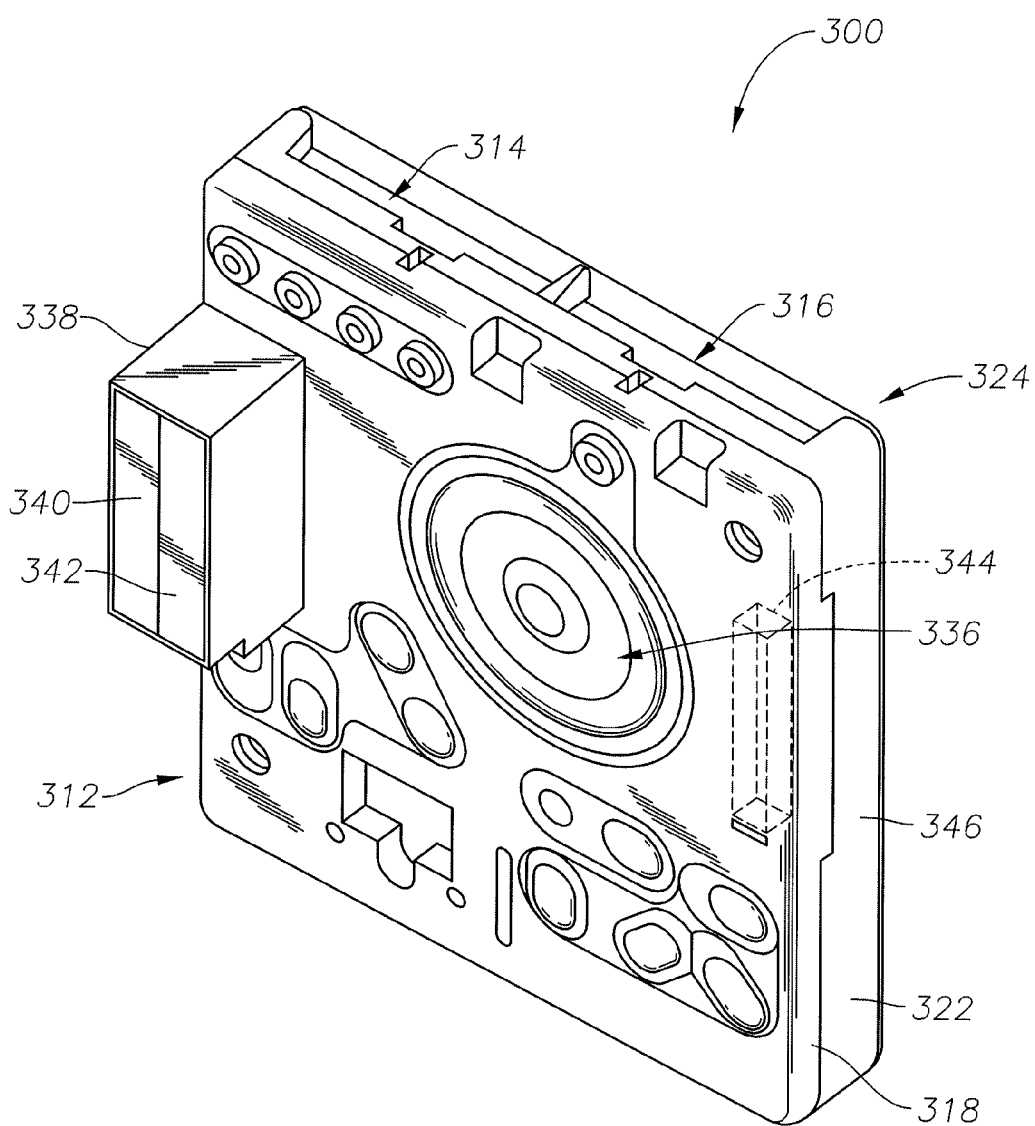
FIG. 3 is a diagrammatic representation of one embodiment of a surgical cassette.

FIG. 2 is a diagrammatic representation of one embodiment of the cassette receiver 132 without a cassette 300 (shown in FIG. 3). The cassette receiver 132 can have various pneumatic input and output ports to interface with the liquid cassette 300. The cassette receiver 132 can further include an opening to allow peristaltic pump rollers 248 to contact the cassette 300 during operation. One embodiment of a peristaltic pump and complimentary cassette is described in U.S. Pat. No. 6,293,926 to Sorensen, which is hereby fully incorporated by reference herein. The cassette receiver 132, is configured to hold the cassette 300 in place by a clamp having a bottom rail 250 and a top rail (not shown). Each rail can have outer clamping fingers (e.g., clamp finger 252) that contact the cassette 300 in corresponding clamping zones and inner clamping fingers to locate the cassette 300 during insertion and push the cassette 300 out of the cassette receiver 132 during release. A release button 254 is pressed to initiate release of the cassette 300 from the clamp. The cassette receiver 132 can include linear light sources 256 and 258. The linear light source 256 projects light onto the walls of the cassette chamber and a sensor array 260 detects the light refracted through the chamber walls. Each of the linear light sources 256 and 258 can include a plurality of light sources vertically arranged (i.e., to project light along vertically spaced transmission paths) and positioned to project light onto a wall of a chamber. Respective linear sensor arrays can receive light refracted through the chamber or reflected at the chamber surface.

The configuration of FIG. 2 is provided by way of example. The form factor of the cassette receiver 132, placement and number of input/output ports and other features of the cassette receiver 132 can depend on the surgical console 100, surgical procedure being performed, or other factors.

In an exemplary embodiment, as illustrated in FIG. 3, a diagrammatic representation of a liquid cassette is generally referred to by the reference numeral 300. The cassette 300 can provide a closed system fluidic device that can be discarded following a surgical procedure. A surgical procedure is generally performed on a human body and typically involves forming a passage through an external surface of the body, but can also be performed through a natural orifice. The cassette 300 can include a cassette body 312 and portions that interface with a clamp (e.g., indicated generally at clamping zones 314 and 316) projecting from the cassette body 312. The cassette 300 can be formed of ABS plastic or other suitable material. In the embodiment shown, the cassette 300 is formed from three primary sections: an inner or surgical console interface section 318 that faces the surgical console 100 when the cassette 300 is inserted into the surgical console 100, a middle section 322, and a cover plate 324. The various sections of the cassette 300 can be coupled together via a press fit, interlocking tabs, chemical bonding, thermal bonding, mechanical fasteners or other attachment mechanisms. In other embodiments, the cassette 300 can be formed of a single piece or multiple pieces.

In operation, the cassette 300 can be placed in the cassette receiver 132. A clamp in the surgical console 100 clamps the cassette 300 in place to minimize movement of the cassette 300 during use. The clamp can clamp the top and bottom of the cassette 300, the sides of the cassette 300 or otherwise clamp the cassette.

The cassette 300 can be configured so that specific operations, such as priming of at least a portion of the cassette 300, can be initiated and/or completed upon selecting a priming instruction option on the GUI or by physically flipping a switch, pressing a button, or the like. For example, an option to automatically complete a priming of the infusion system can be selected by a user on the GUI and the priming of the infusion system will be completed without additional interaction from the user.

The surgical console interface section 318 can face the console 100 during use and provide an interface for liquid flow channels (e.g., flow channel 336 for the peristaltic pump provided by an elastomeric pump membrane), valves (e.g., infusion/aspiration valves), and other features to manage liquid flow. The cassette 300 can also attach to a liquid bag (not shown) to collect liquids during a procedure.

In one embodiment, the liquid cassette 300 includes chambers to hold liquids for aspiration and infusion. For example, chamber cartridge 338 can include infusion chambers 340 and 342. An aspiration chamber 344 can be internal to the cassette 300 on the opposite side of the cassette 300 from the chamber cartridge 338 (e.g., at the side of the cassette 300 indicated by 346). According to one embodiment, the level of liquid in the chambers 340, 342, and 344 can be determined in a noninvasive manner via a level sensor. One embodiment of a non-invasive method of measuring the liquid in the chambers is described in U.S. Pat. No. 7,956,341 to Gao, which is hereby fully incorporated by reference herein.

Figure 4:
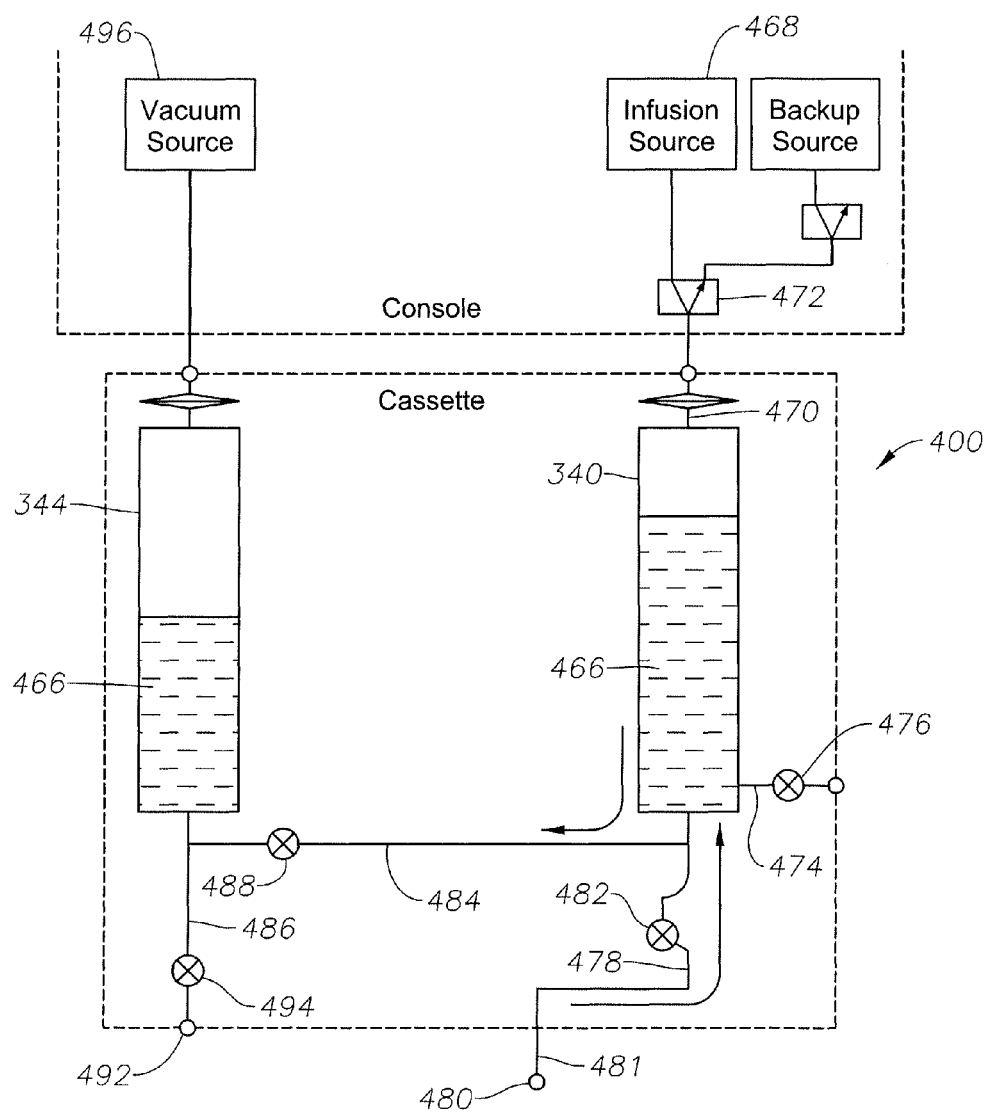
FIG. 4 is diagrammatic representation of an infusion system, according to an exemplary embodiment.

One embodiment of an infusion system, being located at least partially within the liquid cassette 300, is shown in FIG. 4 and is generally referred to by the numeral 400. The infusion system 400 has the infusion chamber 340 configured to hold a liquid 466 and configured to fluidly couple to a infusion pressure source 468 via a conduit 470 having an infusion isolation valve 472. Additionally, the infusion chamber 340 is configured to fluidly couple to a pressurized liquid source (not shown) via a source conduit 474 having a source valve 476. The infusion chamber 340 is also attached to an infusion conduit 478, with one end portion of the infusion conduit 478 connected to the infusion chamber 340 and an opposing end portion having an infusion port 480 configured to attach to a surgical device, such as a cannula, via an infusion tube 481, the infusion conduit 478 including the infusion tube 481. The infusion conduit 478 has an infusion valve 482 positioned between the infusion port 480 and an intersection of the infusion conduit 478 and a cross conduit 484. The cross conduit 484 extends between the infusion conduit 478 and an aspiration conduit 486 and has a cross valve 488. The aspiration conduit 486 is attached to the aspiration chamber 344 and has an aspiration port 492, the aspiration conduit 486 having an aspiration valve 494 located between the aspiration port 492 and the intersection of the cross conduit 484 with the aspiration conduit 486. The aspiration chamber 344 is configured to hold the liquid 466 and configured to fluidly couple with a vacuum source 496.

In one embodiment, the infusion chamber 340 is located above the infusion conduit 478, with at least portions of the infusion conduit 478 running vertically from a lower height near the infusion port 480 towards an upper height near the infusion chamber 340.

The vacuum source 496 may be any suitable device for generating vacuum but is preferably a vacuum chip or a venturi chip. The level sensors may be any suitable device for measuring the level of the liquid 466 within the chambers 340, 342 and 344, but is preferably capable of measuring liquid levels in a continuous manner. The surgical device may be any surgical device that aspirates liquid and/or tissue, but is preferably an ophthalmic surgical device such as a phacoemulsification probe, a vitrectomy probe, an aspiration probe, or cannula. The surgical device (not shown) has a tip with a port that is fluidly coupled to the infusion conduit 478 via the infusion port 480. The liquid 466 may be any suitable infusion liquid, such as, by way of example, BSS PLUS® intraocular irrigating solution available from Alcon Laboratories, Inc. of Fort Worth, Tex.

Figure 5:
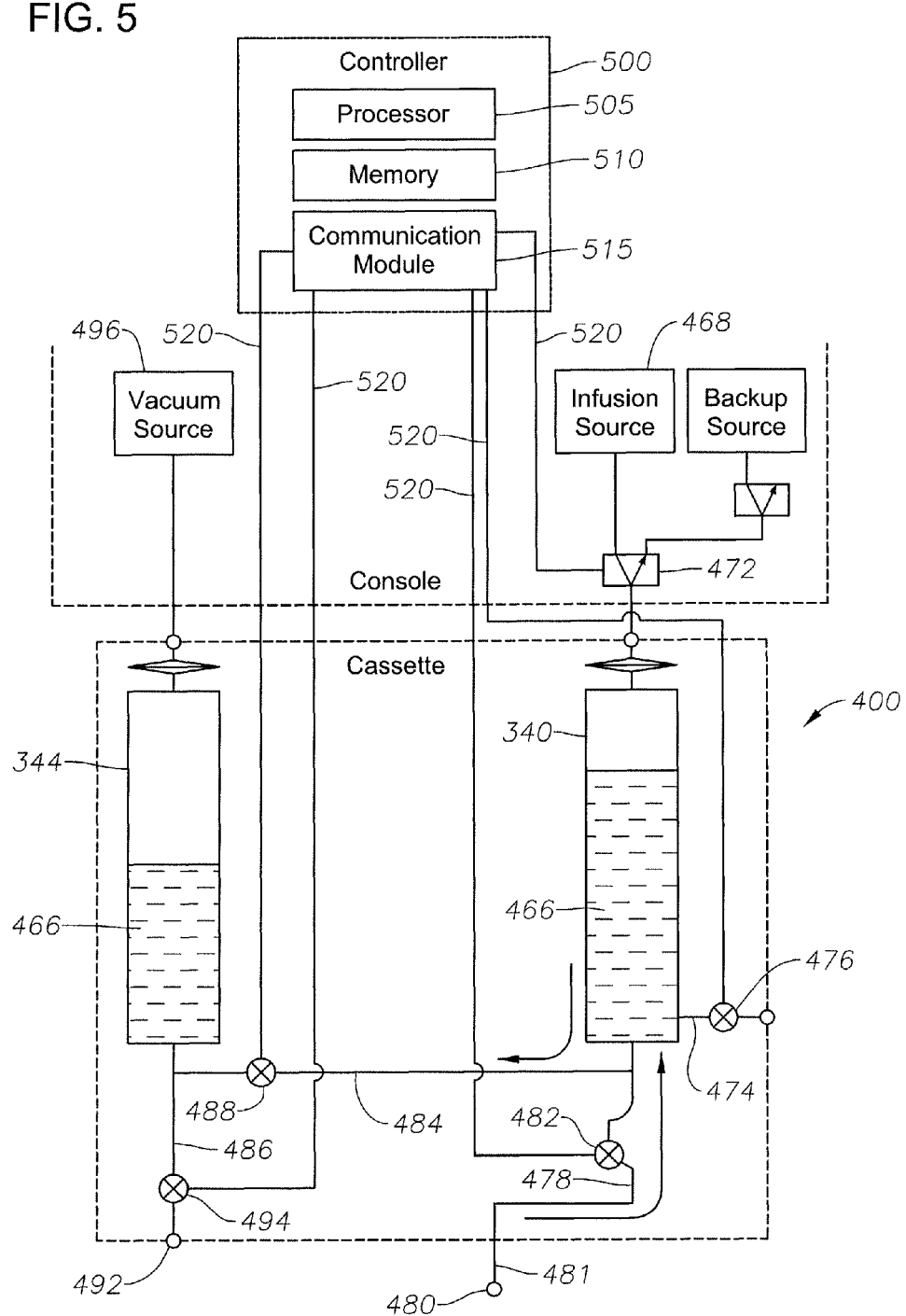
FIG. 5 is a diagrammatic representation of the infusion system, according to an exemplary embodiment.

In one embodiment, as shown in FIG. 5, the system 400 has a controller 500, which includes a processor 505 and a memory 510 coupled thereto. The controller 500 also includes a communication module 515. The communication module 515 is electronically coupled to the valves 472, 476, 482, 488, and 494 via control lines 520. The controller 500 controls the opening and closing of the valves 472, 476, 482, 488, and 494. The controller 500 is capable of implementing feedback control, and preferably is a proportional-integral-derivative controller (PID controller). The controller 500 is also operably coupled to the infusion pressure source 468 and the vacuum source 496 via the control lines 520, and controls the operation of the infusion pressure source 468 and the vacuum source 496. The controller 500 is also operably coupled to the level sensors and receives data from the level sensors.

Figure 6A:
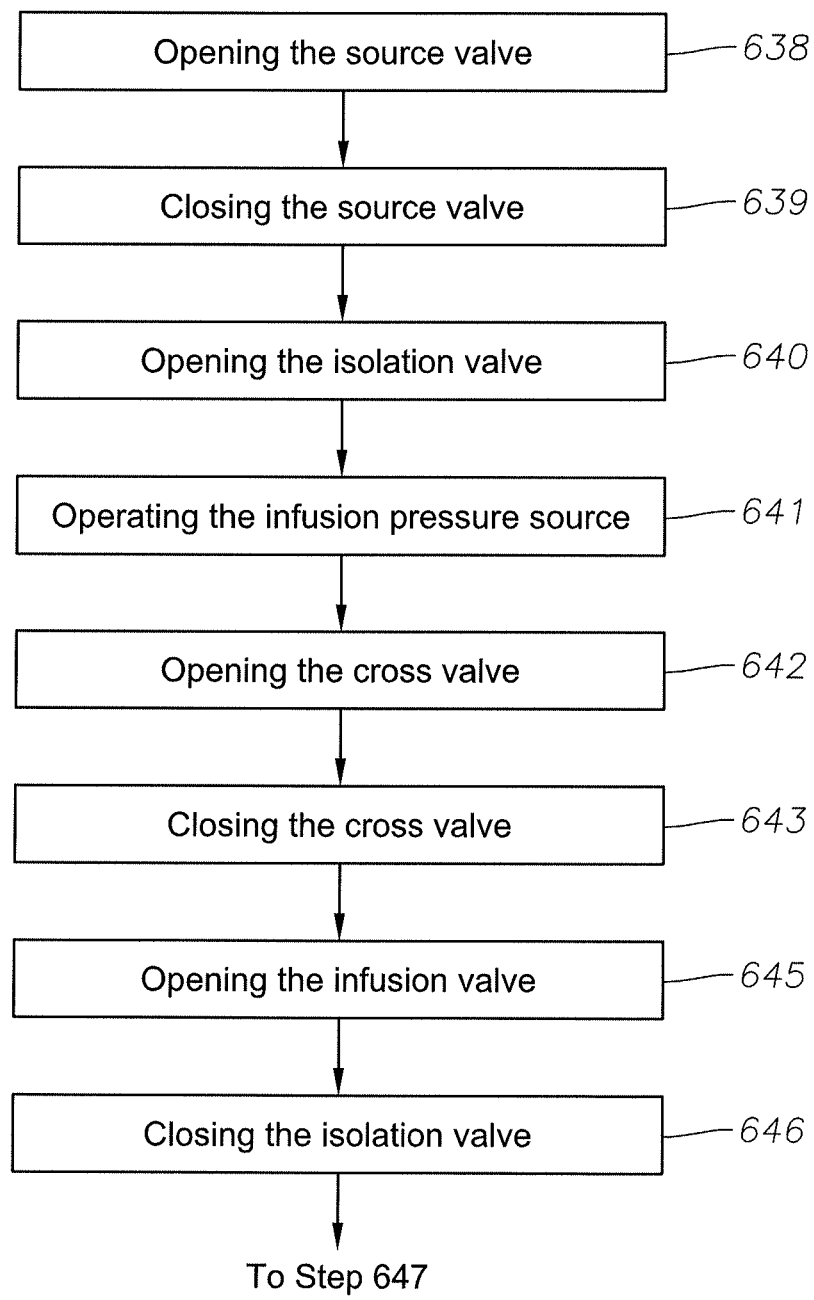
FIG. 6A is a flow chart illustration of a method of operating the system of FIG. 5, according to an exemplary embodiment.

In an exemplary embodiment, as illustrated by the flowcharts in FIGS. 6A and 6B, a method of priming the infusion system 400 is generally referred to by the reference numeral 600. The following describes one method of priming the infusion system 400 of FIG. 5. At step 638, the controller 500 opens the source valve 476 to allow the liquid 466 to enter the infusion chamber 340 and the source conduit 474 from the pressurized liquid source.

At step 639, the controller 500 closes the source valve 476, leaving the infusion chamber 340 containing sufficient fluid 466 to substantially fill the conduits 484, 486, and 478 and the surgical device. The step 639 can occur after a predetermined time or alternatively, the liquid level sensor may signal the controller 500 when a predetermined liquid level within the infusion chamber 340 is reached.

At step 640, the controller 500 opens the isolation valve 472. At step 641, the controller 500 operates the infusion pressure source 468 to pressurize the infusion chamber 340. During the step 641, the valves 476, 482 and 488 are closed, allowing pressure to build in the infusion chamber 340. At step 642, the controller 500 opens the cross valve 488, resulting in a high pressure forward flow of the liquid 466 from the infusion chamber 340 towards the aspiration chamber 344 through the cross conduit 484, the aspiration conduit 486 and the cross valve 488. At step 643, the controller 500 closes the cross valve 488. At step 645, the controller 500 opens the infusion valve 482, resulting in a high pressure forward flow of the liquid 466 from the infusion chamber 340 towards the infusion port 480 through the infusion conduit 478 and the infusion valve 482. The infusion pressure source 468 pushes the infusion liquid 466 from the infusion chamber 340. A portion of the infusion conduit 478 is filled with a first volume of the liquid 466 to create a reservoir of the fluid 466. In one embodiment, the first volume or reservoir of the liquid 466 in the infusion conduit 478 can be a volume of between 10 to 20 cubic centimeters. The surgical device and the tip of the surgical device are also filled with the liquid 466, with the tip exposed to a non-liquid atmosphere having a first pressure. Gas, such as air, can become trapped within the conduits 474, 478, 484, and 486 and around or in the valves 482, 488 and 494. This application of high pressure to the liquid 466 can compress the size of any trapped gas and therefore make the removal of the trapped gas difficult. Additionally, due to the infusion chamber 340 being located above the infusion conduit 478, any buoyancy force associated with the gas trapped in the infusion conduit 478 pulls the gas vertically upwards through the infusion conduit 478 and towards the surface of the liquid 466 in the infusion chamber 340. The forward flow of the liquid 466 towards the infusion port 480 caused by the operation of the infusion pressure source 468 is meant to flush the gas from the infusion conduit 478, however the buoyancy force of the gas acts to resist from being flushed away by the forward flow of the liquid 466 and gas can remain in the infusion conduit 478. Additionally, the tip of the surgical device generally has a very small diameter, therefore when pressure is applied to the liquid 466 within the infusion conduit 478, a low forward flow results in the infusion conduit 478. The diameter of the tip of the surgical device can be approximately 25 gauge. The steps 638-645 can be omitted if desired and replaced with steps for any conventional method of priming an infusion system 400 using forward flow of the liquid 466.

At step 646, the controller 500 closes the isolation valve 472. The valves 482, 488, and 476 remain closed. Closing the isolation valve 472 isolates the infusion chamber 340.

At step 647, the controller 500 activates the vacuum source 496 to create a second pressure within the aspiration chamber 344 and within at least a portion of the cross conduit 484. The second pressure is lower than the first pressure associated with the non-liquid atmosphere at the tip of the surgical device. Due to the valves 494 and 488 being closed, the vacuum source 496 creates the second pressure within the aspiration conduit 486 in the section between the aspiration valve 494 and the aspiration chamber 344 and within the cross conduit 484 in the section between the cross valve 488 and the aspiration chamber 344.

At steps 648 and 650, the controller 500 momentarily opens the cross valve 488 to create the second pressure within the infusion chamber 340. A second volume of the liquid 466, which is the necessary volume of the liquid 466 that would equalize the pressure of the infusion chamber 340 and the first pressure, can be determined. In one embodiment, the second volume of the liquid 466 is between 5 to 8 cubic centimeters.

At step 652, the controller 500 opens the infusion valve 482 causing the second volume of the liquid 466 to flow over the infusion valve 482. The second volume of the liquid 466 flows away from the tip of the surgical device (associated with the first pressure) and towards the infusion chamber 340 (associated with a lower, second pressure). The second volume of the liquid 466 is less than or equal to the first volume of the liquid 466. A volume of a non-liquid in the non-liquid atmosphere that is in contact with the tip of the surgical device is drawn into the surgical device to replace the second volume of the liquid 466 that is being drawn towards the infusion chamber 340. In one embodiment, the non-liquid can be any gas or gaseous mixture. Due to the second volume of the liquid 466 being equal to or less than the first volume of the liquid 466, the non-liquid is not drawn into the cassette 300. In one embodiment, the non-liquid is only drawn into a portion of the infusion conduit 478 located outside of the cassette 300. This liquid flow, in a direction away from the tip of the surgical device or away from the infusion port 480 and towards the infusion chamber 340, is considered a reverse flow. This reverse flow results in the liquid 466 flowing in the same direction (vertically towards the infusion chamber 340) as the buoyancy force of any trapped gas, therefore, the trapped gas is encouraged to flow towards and into the infusion chamber 340, where the gas then escapes to the infusion chamber 340 and can be removed. Additionally, exposing the liquid 466 to the second pressure, which is lower than the first pressure, allows for the trapped gas to expand, therefore making the trapped gas easier to dislodge than when pressurized into a smaller volume during the forward flow.

At step 654, the controller 500 pulses the infusion valve 482 from an open position to a closed position. The step 654 is optional, and may be omitted if desired. The purpose of the step 654 is to create a transient flow of the liquid 466 and dislodge trapped gas located near or within the infusion valve 482.

Steps 656, 658, and 660 result in a pressurized forward flow of the liquid 466 in the system 400. In one embodiment, at the step 656, the controller 500 deactivates the vacuum source 496. This step 656 may be omitted if the vacuum source 496 has already been deactivated or if the vacuum source 496 has otherwise been isolated from the system 400. At the step 658, the controller 500 opens the infusion valve 482 and the isolation valve 472. At the step 660, the controller 500 activates the infusion pressure source 468, resulting in a high pressure forward flow of the liquid 466 from the infusion chamber 340 towards the infusion port 480 through the infusion conduit 478. This ensures that the infusion conduit 478 and the infusion valve 482 are filled with the liquid 466. The steps 656, 658, and 660 may be omitted if desired and replaced with any conventional method of causing a forward liquid flow in the system 400.

Figure 6C:
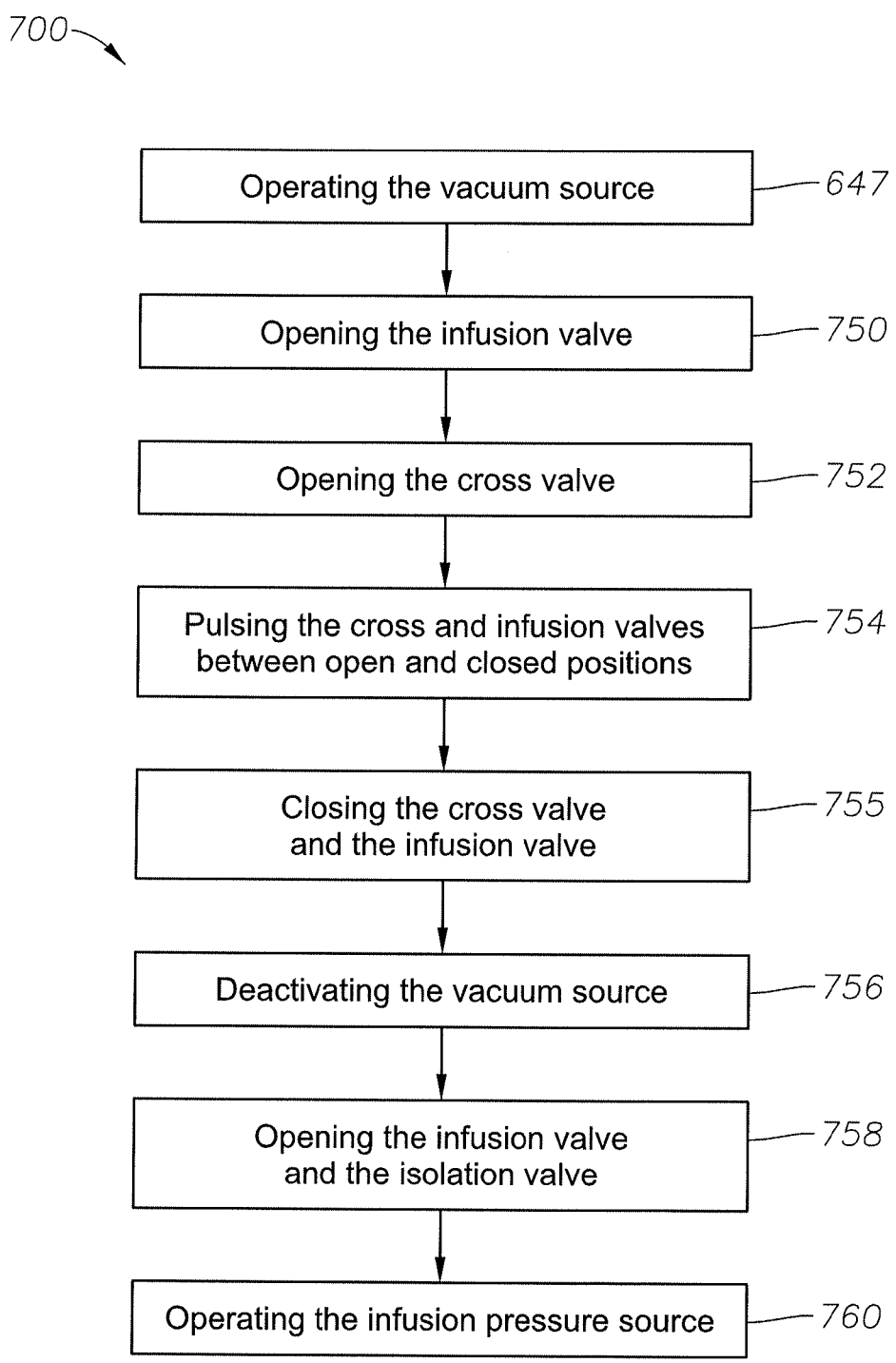
FIG. 6C is a flow chart illustration of a method of operating the system of FIG. 5, according to an exemplary embodiment.

In an exemplary embodiment, as illustrated in FIGS. 6A and 6C, a method of operating the system 400 is generally referred to by the reference numeral 700. The method 700 includes the steps 638-643 and 645-647, but does not include the steps 648, 650, 652, 654, 656, 658, and 660 of the method 600. Instead, after the step 647 of the method 700, the controller 500 opens the infusion valve 482 at the step 750. At the step 752 the controller 500 opens the cross valve 488. The opening of the valves 482 and 488 allows for the second volume of the liquid 466 contained within the infusion conduit 478 to move across the infusion valve 482 in a reverse flow towards the aspiration chamber 344 instead of into the infusion chamber 340.

At the step 754, the controller 500 pulses the infusion valve 482 and the cross valve 488 from an open position to a closed position. The step 754 is optional, and may be omitted if desired. The purpose of the step 754 is to create a transient flow of the liquid 466 and dislodge trapped gas located near or within the infusion valve 482 and the cross valve 488. At the step 755, the cross valve 488 and the infusion valve 482 are closed.

The steps 756, 758, and 760 are substantially similar to the steps 656, 658, and 660, respectively, and therefore will not be discussed in detail. Similarly to the steps 656, 658, and 660, one or all of the steps 756, 758, and 760 may be omitted if desired. The steps 756, 758, and 760 may be replaced with any conventional method of causing a forward liquid flow in the system 400.

In one embodiment, the infusion system 400 as shown in FIG. 4 can be primed by the method 600 or the method 700 without the assistance of a controller 500. Any and all steps may be performed manually.

The reverse flow, as described above, can result in a higher flow rate than a flow rate associated with the forward flow. This is because, as described above, the fluid 466 interaction with the small diameter of the tip of the surgical device prohibits a high forward flow rate. However, with a reverse flow, the non-liquid atmosphere is entering the tip of the surgical device and results in a flow rate within the infusion conduit 478 higher than the flow rate in the infusion conduit 478 associated with the fluid 466 flowing towards the tip of the surgical device. Additionally, the infusion pressure source 468 may be limited to operate with a maximum pressure of approximately 120 mmHg due to safety concerns. However, the vacuum source 496 can operate at a maximum vacuum of approximately 650 mmHg, resulting in a higher potential pressure differential within the system 400 during reverse flow.

In one embodiment, the valves 476, 482, 488, and 494 can be at least partially located on the cassette 300. In one embodiment, at least a portion of the infusion conduit 478, such as the infusion tube 481, is located outside of the cassette 300. In one embodiment, a command from a user to prime the infusion system 400 can be received through the GUI on the console 100 and the controller 500 can prime the infusion system 400 using the method 600 or the method 700 without further interaction from the user.

It is understood that variations may be made in the foregoing without departing from the scope of the present disclosure.

In several exemplary embodiments, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several exemplary embodiments, while different steps, processes, and procedures are described as appearing as distinct acts, one or more of the steps, one or more of the processes, and/or one or more of the procedures may also be performed in different orders, simultaneously and/or sequentially. In several exemplary embodiments, the steps, processes and/or procedures may be merged into one or more steps, processes and/or procedures.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures.

What is claimed is:

1. A method of priming an infusion system, comprising:
providing a system having an infusion chamber provided with an infusion liquid, the infusion chamber connected to an infusion conduit having a first valve, the system having a cross conduit intersecting the infusion conduit at a location between the infusion chamber and the first valve, the cross conduit coupled to an aspiration chamber, the cross conduit having a second valve, the aspiration chamber coupled to a vacuum source;
filling the infusion conduit with a first volume of the infusion liquid, the infusion conduit having an infusion port exposed to a non-liquid environment having a first pressure;
closing the first and second valves to isolate the infusion chamber;
operating the vacuum source to create a second pressure in the aspiration chamber that is lower than the first pressure;
opening the first valve and the second valve to produce a second volume of the infusion liquid in the infusion conduit to flow over the first valve towards the infusion chamber; and
wherein the second volume of the infusion liquid is less than or equal to the first volume of the infusion liquid.

2. The method of claim 1, wherein opening the first valve and the second valve to produce the second volume of the infusion liquid in the infusion conduit to flow over the first valve comprises:
opening the second valve to create the second pressure in the infusion chamber;

closing the second valve to isolate the infusion chamber at the second pressure; and after opening and closing the second valve, opening the first valve to allow the second volume of the infusion liquid to flow over the first valve.

3. The method of claim 1, wherein opening the first valve and the second valve to produce the second volume of the infusion liquid in the infusion conduit to flow over the first valve comprises:

opening the first valve; and after opening the first valve, opening the second valve to allow the second volume of the infusion liquid in the infusion conduit to flow over the first valve.

4. The apparatus of claim 1, wherein the first volume of the liquid is between 10 and 20 cubic centimeters and the second volume of the liquid is less than or equal to 10 cubic centimeters.

5. The method of claim 1, further comprising the steps of:

providing a controller electronically coupled to the first valve, the second valve, and the vacuum source; and wherein the controller controls the opening and closing of the first valve and the second valve and the controller controls the operation of the vacuum source.

6. The method of claim 1, wherein the infusion port is configured to fluidly couple with a device and wherein a non-liquid in the non-liquid environment enters the device as the second volume of the infusion liquid moves over the first valve.

7. A method of operating an infusion system, comprising:

providing a system having an infusion chamber, the infusion chamber connected to an infusion conduit having a first valve, the infusion conduit having an infusion port exposed to a non-liquid environment having a first pressure;

wherein the infusion chamber is coupled to an infusion pressure source via an isolation valve;

wherein the infusion chamber is fluidly coupled to an aspiration chamber via a cross conduit, the cross conduit intersecting the infusion conduit at a location between the infusion chamber and the first valve, the cross conduit having a second valve;

wherein the infusion chamber is fluidly coupled with a liquid source via a source conduit having a source valve; and wherein the aspiration chamber is fluidly coupled with a vacuum source;

controlling the system to open the source valve and the second valve;

controlling the system to close the source valve;

controlling the system to open the first valve, the second valve, and the isolation valve;

controlling the system to operate the infusion pressure source to push the liquid from the infusion chamber, thereby filling the infusion conduit with a first volume of liquid;

controlling the system to close the first valve, the second valve, and the isolation valve to isolate the infusion chamber;

controlling the system to operate the vacuum source, thereby creating a second pressure in the aspiration chamber, the second pressure being lower than the first pressure;

controlling the system to open the first valve and the second valve to produce a second volume of the liquid to flow over the first valve; and wherein the second volume of the liquid is less than or equal to the first volume of the liquid.

8. The method of claim 7, wherein controlling the system to open the first valve and the second valve to produce the second volume of the liquid to flow over the first valve comprises:

opening the second valve to create the second pressure within the infusion chamber;

closing the second valve to isolate the infusion chamber at the second pressure; and opening the first valve to allow the second volume of the liquid to flow over the first valve.

9. The method of claim 7, wherein controlling the system to open the first valve and the second valve to produce the second volume of the liquid to flow over the first valve comprises:

opening the first valve; and opening the second valve to allow the second volume of the liquid to flow over the first valve.

10. The method of claim 7 further comprising the step of controlling the system to rapidly open and close the first valve and the second valve to create a transient flow of the liquid.

11. The method of claim 7, wherein the infusion port is configured to fluidly couple with a device and wherein a non-liquid in the non-liquid environment enters the device as the second volume of the liquid moves over the first valve.

12. The method of claim 7, further comprising the steps of:

controlling the system to open the first valve and the isolation valve; and controlling the system to activate the infusion pressure source to push the liquid away from the infusion chamber and towards the infusion port.

13. The method of claim 7, further comprising the steps of:

providing a controller electronically coupled to the first valve, the second valve, the source valve, the isolation valve, the infusion pressure source, and the vacuum source via control lines; and wherein the controller controls the opening and closing of the first valve, the second valve, the source valve, and the isolation valve and the controller controls the operation of the infusion pressure source and the vacuum source.

14. The apparatus of claim 7, wherein the first volume of the liquid is between 10 and 20 cubic centimeters and the second volume of the liquid is less than or equal to 10 cubic centimeters.

* * * * *